(12) United States Patent
Tu et al.

(10) Patent No.: US 10,119,915 B2
(45) Date of Patent: Nov. 6, 2018

(54) DETECTION DEVICE FOR SPECIMENS

(71) Applicant: VisEra Technologies Company Limited, Hsin-Chu (TW)

(72) Inventors: Zong-Ru Tu, Keelung (TW); Chin-Chuan Hsieh, Hsin-Chu (TW); Wei-Ko Wang, Taoyuan (TW)

(73) Assignee: VISERA TECHNOLOGIES COMPANY LIMITED, Hsin-Chu (TW)

( * ) Notice: Subject to any disclaimer, the term of this patent is extended or adjusted under 35 U.S.C. 154(b) by 250 days.

(21) Appl. No.: 14/682,580

(22) Filed: Apr. 9, 2015

(65) Prior Publication Data

US 2016/0299073 A1  Oct. 13, 2016

(51) Int. Cl.
| H04N 7/18 | (2006.01) |
| G01N 21/64 | (2006.01) |
| C12Q 1/6869 | (2018.01) |

(52) U.S. Cl.
CPC ....... G01N 21/648 (2013.01); G01N 21/6452 (2013.01); C12Q 1/6869 (2013.01)

(58) Field of Classification Search
CPC .................................................. G01N 21/648
See application file for complete search history.

(56) References Cited

U.S. PATENT DOCUMENTS

| 6,580,081 B1 | 6/2003 | Thorwirth |
| 7,170,605 B2 | 1/2007 | Cromwell et al. |
| 8,003,983 B2 | 8/2011 | Yu |
| 8,314,469 B2 | 11/2012 | Yu |
| 2002/0182111 A1 | 12/2002 | Feygin |
| 2005/0237524 A1 | 10/2005 | Kamei et al. |
| 2007/0045513 A1 | 3/2007 | Lee et al. |
| 2009/0311774 A1 | 12/2009 | Chiou |
| 2010/0025567 A1 | 2/2010 | Lueerssen |
| 2010/0065726 A1 | 3/2010 | Zhong et al. |
| 2010/0096561 A1 | 4/2010 | Johnson |
| 2011/0108938 A1 | 5/2011 | Nozaki et al. |
| 2011/0223590 A1 | 9/2011 | Chiou |

(Continued)

FOREIGN PATENT DOCUMENTS

| CN | 101960293 A | 1/2011 |
| CN | 102713572 A | 10/2012 |

(Continued)

OTHER PUBLICATIONS

The Office Action with the search report of corresponding TW application No. 105108637 dated Feb. 15, 2017.

(Continued)

*Primary Examiner* — Leron Beck
(74) *Attorney, Agent, or Firm* — Muncy, Geissler, Olds & Lowe, P.C.

(57) ABSTRACT

A detection device for specimens includes an image sensor, a light-guiding structure, a carrier, and a light source. The light-guiding structure is disposed on the image sensor, and includes a light-guiding layer and a top layer. The light-guiding layer is disposed on the image sensor. The top layer is disposed on the light-guiding layer. The carrier is disposed on the light-guiding structure. The carrier has a number of wells arranged in an array located over the guiding portions. Each of the wells is configured to receive a specimen.

16 Claims, 8 Drawing Sheets

(56) References Cited

U.S. PATENT DOCUMENTS

| | | | |
|---|---|---|---|
| 2011/0250690 A1* | 10/2011 | Craig | A01N 1/02 |
| | | | 435/404 |
| 2011/0306039 A1 | 12/2011 | Chiou et al. | |
| 2011/0306143 A1 | 12/2011 | Chiou | |
| 2012/0142086 A1 | 6/2012 | Haguet et al. | |
| 2012/0224053 A1 | 9/2012 | Vykoukal et al. | |
| 2013/0143206 A1 | 6/2013 | McCaffrey et al. | |

FOREIGN PATENT DOCUMENTS

| | | |
|---|---|---|
| CN | 103348668 A | 10/2013 |
| JP | 2005283568 A | 10/2005 |
| JP | 2011512641 A | 4/2011 |
| JP | 2013524174 A | 6/2013 |
| TW | M249381 U | 11/2004 |
| TW | 200936765 A | 9/2009 |
| TW | 201017163 A | 5/2010 |
| WO | WO 2011/153962 A1 | 12/2011 |

OTHER PUBLICATIONS

JP Office Action with its English translation dated Jul. 5, 2016 in application No. 2015-189199, pp. 1-6.

Office Action of U.S. Appl. No. 14/878,272 dated Jul. 11, 2017 (23 pages).

Office Action dated May 31, 2018 in CN Application No. 201610180391.9 (8 pages).

* cited by examiner

DETECTION DEVICE FOR SPECIMENS

BACKGROUND OF THE INVENTION

Field of the Invention

The present disclosure relates to a detection device, and in particular to a detection device for specimens.

Description of the Related Art

Various biochips, such as microfluidic chips, micro-array chips, or lab-on-a-chips, have been developed to detect human genome, and thus the research of sequencing human genome has been great improved. A person's blood can be analyzed to check whether the blood contains a biomarker for a specific disease. That is how so as a genetic diseases can be detected.

Figure 1:
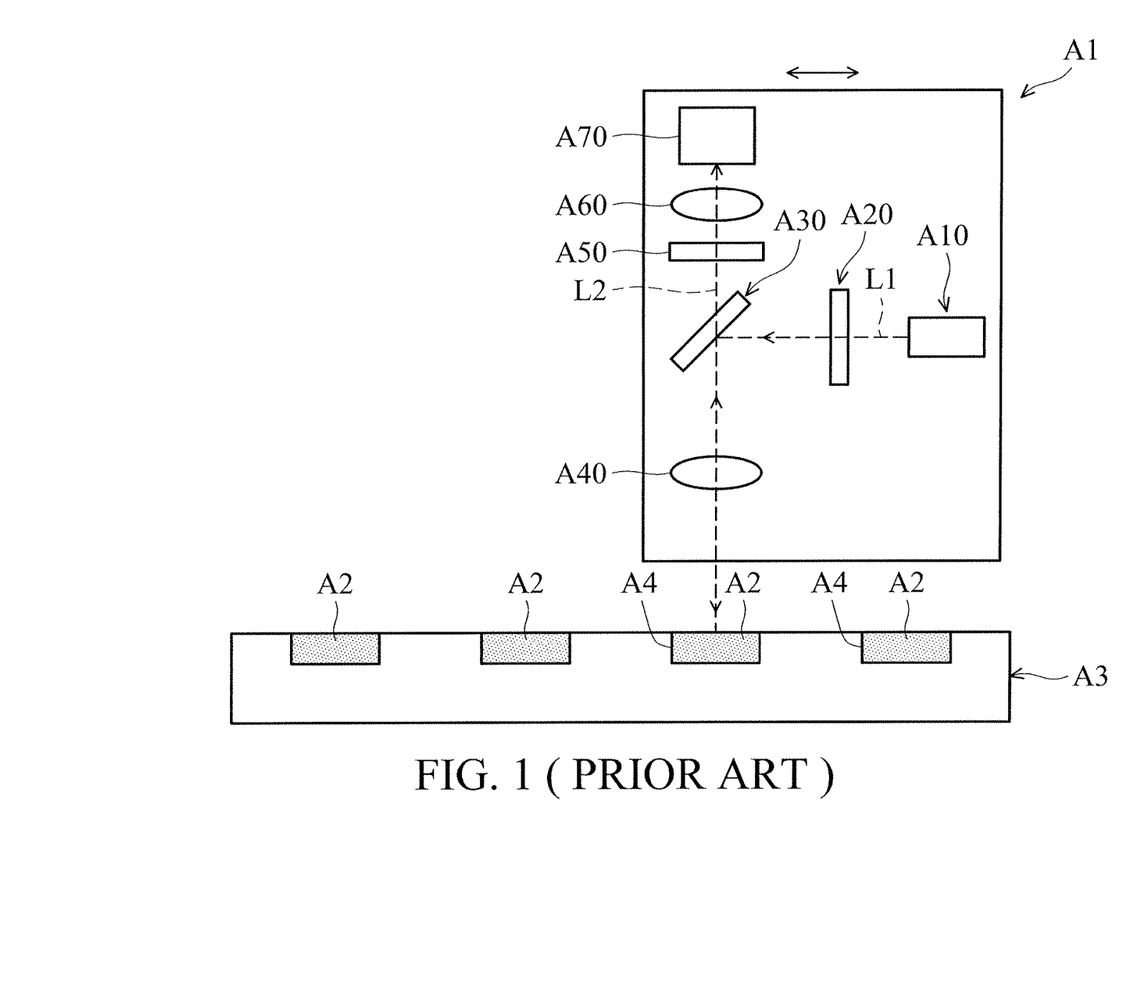
FIG. 1 is a schematic diagram of a conventional biochip detection device.

FIG. 1 is a schematic diagram of a conventional biochip detection device A1. The biochip detection device A1 is used for detecting specimens A2 carried on a biochip A3. The biochip A3 includes a number of wells A4 arranged in an array for receiving the specimens A2. The biochip detection device A1 includes a laser source A10, a filter A20, a beam splitter A30, a lens A40, a filter A50, a lens A60 and a detector A70.

The laser source A10 emits an excitation beam L1 toward the beam splitter A30. The filter A20 is located between the laser source A10 and the beam splitter A30 and is used for filtering the excitation beam L1 with a desired wavelength. For example, the wavelength of the excitation beam L1 is in a range from about 300 nm to 500 nm. The beam splitter A30 reflects the excitation beam L1 to the specimen A2. The lens A40 focuses the excitation beam L1 on the specimen A2.

After the specimen A2 is irradiated by the excitation beam L1, the specimen emits an induced beam L2 to the filter A50 by passing through the beam splitter A30. In general, the induced beam L2 is a fluorescence beam. The filter A50 is for blocking the excitation beam L1, since a portion of the excitation beam L1 may pass through the beam splitter A30 to the detector A70.

The lens A60 is for focusing the induced beam L2 on the detector A70. The detector A70 is for analyzing the wavelength and the strength of the induced beam L2. However, since the excitation beam L1 and the induced beam L2 have the same optical path, the induced beam L2 detected by the detector A70 is distributed by the excitation beam L1. Therefore, thus the detection result of the specimen A2 is influenced.

The conventional biochip detection device A1 detects the specimen in a point-by-point manner, thus it will be very time-consuming whenever it scans a biochip A3 with numerous specimens A2.

Moreover, as shown in FIG. 1, the conventional biochip detection device A1 includes a large amount of optical elements, and a transport device is also needed to move the biochip detection device A1 for detecting the specimens A2 in sequence. Therefore, the size and the weight of the biochip detection device A1 is great, and the manufacturing cost of the biochip detection device A1 is expensive. The biochip detection device A1 is not portable or affordable for users.

Although biochip detection devices have been generally adequate for their intended purposes, they have not been entirely satisfactory in all respects. Consequently, it is desirable to provide a solution for improving biochip detection devices.

BRIEF SUMMARY OF THE INVENTION

The present disclosure provides detection device for specimens with a small size and a light weight for portability. Moreover, the manufacturing cost of the detection device is decreased, and the time required for detection of the specimens is also decreased.

The present disclosure provides a detection device for specimens, including an image sensor, a light-guiding structure, a carrier, and a light source. The light-guiding structure is disposed on the image sensor, and includes a light-guiding layer and a number of guiding portions. The light-guiding layer is disposed on the image sensor. The guiding portions are disposed on the light-guiding layer and arranged in an array. The carrier is disposed on the light-guiding structure. The carrier has a number of wells arranged in an array located over the guiding portions. Each of the wells is configured to receive a specimen.

The light source is disposed on a side surface of the light-guiding layer and configured to emit an excitation beam into the light-guiding layer. The excitation beam is transmitted to the specimens via the guiding portions. The specimens emit induced beams when the specimens are irradiated by the excitation beam, and the induced beams are transmitted to the image sensor via the guiding portions and the light-guiding layer in sequence.

The present disclosure provides a detection device for specimens, including an image sensor, a light-guiding structure, a carrier, and a light source. The image sensor includes a number of microlenses arranged in an array. The light-guiding structure includes a light-guiding layer disposed on the microlenses, a top layer disposed on the light-guiding layer, and a transmitting layer disposed on the top layer. The carrier is disposed on the transmitting layer. The carrier has a number of wells arranged in an array. Each of the wells is configured to receive a specimen. The light source is disposed on a side surface of the transmitting layer and is configured to emit an excitation beam into the transmitting layer.

The microlenses are configured to reflect the excitation beam toward the wells via the guiding portions, and the top layer is configured to reflect the excitation beam in the light-guiding layer. The specimens emit induced beams when the specimens are irradiated by the excitation beam, and the induced beams are transmitted to the image sensor via the transmitting layer, the top layer, and the light-guiding layer in sequence.

In conclusion, since the detection device is integrated with the image sensor and the light-guiding structure, the size and the weight of the detection device are greatly decreased, and the manufacturing cost of the detection device is cheap. Moreover, the specimens on the carrier can be detected by the image sensor at the same time, and the thus the time required for detection of the specimens is decreased.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following disclosure provides many different embodiments, or examples, for implementing different features of the present disclosure. Specific examples of components and arrangements are described below to simplify the present disclosure. For example, the formation of a first feature over or on a second feature in the description that follows may include embodiments in which the first and second features are formed in direct contact, and may also include embodiments in which additional features may be formed between the first and second features, such that the first and second features may not be in direct contact.

In addition, the present disclosure may repeat reference numerals and/or letters in the various examples. This repetition is for the purpose of simplicity and clarity and does not in itself dictate a relationship between the various embodiments and/or configurations discussed. Furthermore, the shape, size, and thickness in the drawings may not be drawn to scale or simplified for clarity of discussion; rather, these drawings are merely intended for illustration.

Figure 2:
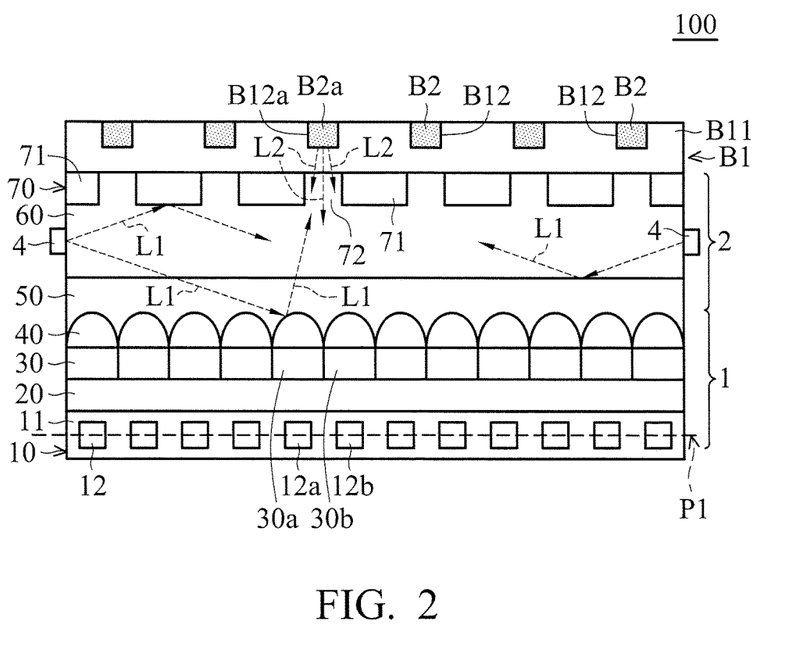
FIG. 2 is a schematic view of a detection device in accordance with a first embodiment of the present disclosure.
Figure 3:
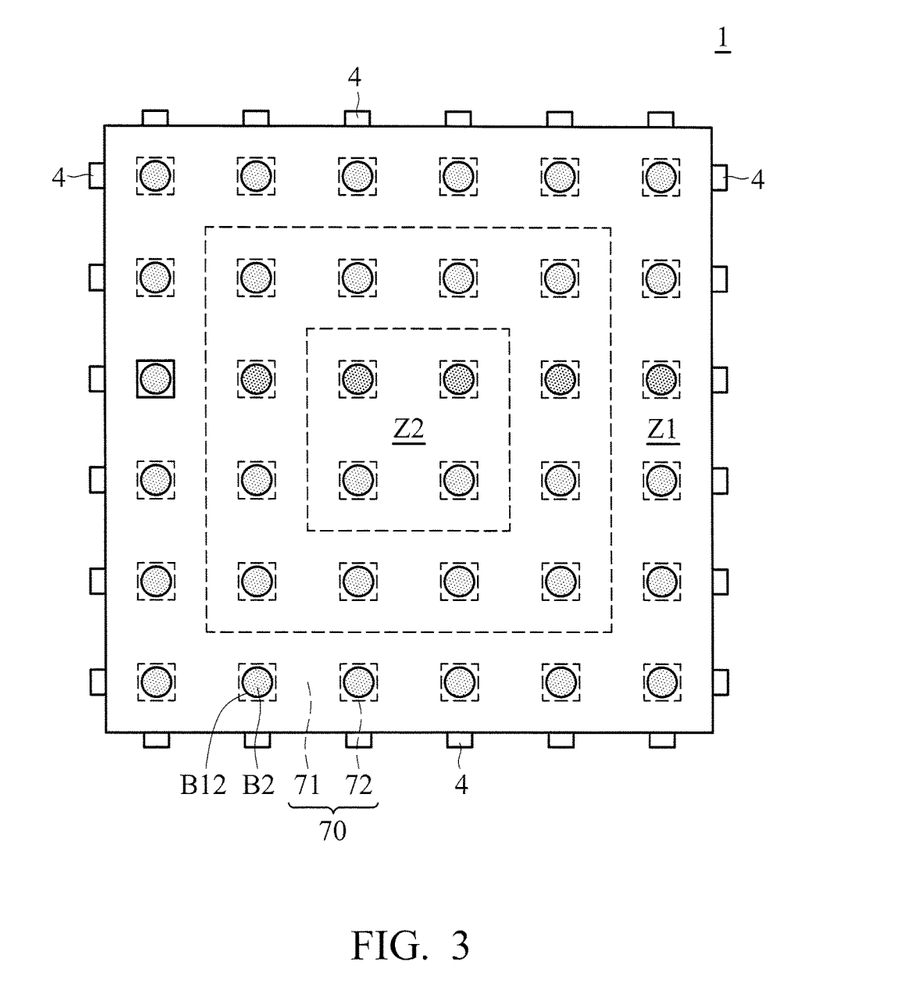
FIG. 3 is a top view of the detection device in accordance with the first embodiment of the present disclosure.

FIG. 2 is a schematic view of a detection device 100 in accordance with a first embodiment of the present disclosure. FIG. 3 is a top view of the detection device 100 in accordance with the first embodiment of the present disclosure. The detection device 100 includes an image sensor 1, a light-guiding structure 2, and light sources 4. The light-guiding structure 2 is disposed on the image sensor 1, and a carrier B1 is disposed on the light-guiding structure 2.

The carrier B1 may be a biochip, such as a microfluidic chip, a micro-array chip, or a lab-on-a-chip. In this embodiment, the carrier B1 is a micro-array chip. In some embodiments, the carrier B1 is detachably disposed on the light-guiding structure 2. In some embodiments, the carrier B1 is fixed at and integrated with the light-guiding structure 2.

The carrier B1 is a plate structure, and includes a carrying body B11 and a number of wells B12 formed on the carrying body B11 and arranged in an array. In some embodiments, the carrying body B11 is made from transparent material, such as glass. Each of the wells B12 is configured to receive a specimen B2. In some embodiments, the specimen B2 includes blood, biological tissue, or DNA fragmentations.

The light sources 4 are disposed on side surfaces of the light-guiding structure 2, and are configured to emit excitation beams L1. In some embodiments, the light sources 4 are laser sources, or LEDs (Light-Emitting Diodes). The wavelength of the excitation beam L1 is in a range from about 200 nm to 500 nm. In other words, the excitation beam L1 is a blue light beam or an ultraviolet light beam.

The light-guiding structure 2 is configured to transmit and guide the excitation beam L1 to the specimen B2 by passing through the carrying body B11. When the specimens B2 are irradiated by the excitation beam L1, the specimens B2 emit induced beams L2 to the image sensor 1. In some embodiments, the induced beams L2 are fluorescence beams.

The image sensor 1 may be a CMOS (Complementary Metal-Oxide-Semiconductor) image sensor, a CCD (charge-coupled device) image sensor, or a SPAD (single-photon avalanche diode) image sensor. The image sensor 1 is manufactured by a semiconductor manufacturing process.

The image sensor 1 is a plate structure, and includes a sensing layer 10, a cutting layer 20, a number of filter units 30, and a number of microlenses 40. The sensing layer 10 extends along a reference plane P1. The sensing layer 10 is configured to sense the induced beams L2 and generate detection signals according to the induced beams L2 falling on the sensing layer 10.

The sensing layer 10 may include all of the following elements, but the sensing layer 10 does not necessarily need to include all of the following elements since the objective of the sensing layer 10 is achieved. The sensing layer 10 includes a substrate 11 and a number of sensing units 12. In some embodiments, the sensing layer 10 further includes other optional layers (not shown in figures).

The sensing units 12 are disposed in the substrate 11. The sensing units 12 are arranged in an array at the reference plane P1. In some embodiments, the sensing units 12 are photodiodes. Each of the sensing units 12 is configured to sense the induced beam L2 and generate a detection signal according to the induced beam L2 falling thereon.

The cutting layer 20 is disposed between the sensing layer 10 and the microlenses 40. In some embodiments, the cutting layer 20 is disposed between the sensing layer 10 and the filter units 30. The cutting layer 20 is configured to block the excitation beam L1 passing through to the sensing layer 10.

The filter units 30 are disposed on the sensing layer 10. The filter units 30 are arranged in an array on a plane parallel to the reference plane P1. Each of the filter units 30 20 is located over one of the sensing units 12.

Each of the filter units 30 allows a predetermined range of wavelengths of light to pass. In some embodiments, the filter units 30 are color filter units 30. For example, the filter units 30 include a number of red filter units 30a and a number of filter units 30b. The red filter units 30a and the filter units 30b are arranged alternately in an array.

The red filter units 30a allow wavelengths of induced beam L2 in a range from 620 nm to 750 nm (red light) to pass to the sensing unit 12. The filter units 30b allow wavelengths of light in a range from 590 nm to 620 nm to pass to the sensing unit 12.

The microlenses 40 are disposed on the filter units 30 and arranged in an array at a plane parallel to the reference plane P1. Each of the microlenses 40 is located over one of the filter units 30. The microlenses 40 are configured to focus the light to the sensing units 12. The microlenses 40 are also configured to reflect the excitation beam L1 toward the wells B12 via the guiding portions 72.

The light-guiding structure 2 is a plate structure parallel to the image sensor 1 and the carrier B1. In some embodiment, the light-guiding structure 2 is made by a semiconductor manufacturing process. The light-guiding structure 2 is integrated with the image sensor 1.

The light-guiding structure 2 includes a bottom layer 50, a light-guiding layer 60, and a top layer 70. The bottom layer 50, the light-guiding layer 60, and the top layer 70 are parallel to the reference plane P1 and are transparent. The bottom layer 50 is disposed on the microlenses 40 of the image sensor 1. In some embodiments, the bottom layer 50 is connected to the microlenses 40.

The light-guiding layer 60 is disposed on the bottom layer 50. As shown in FIGS. 2 and 3, the light sources 4 are disposed on the side surfaces of the light-guiding layer 60, and configured to emit excitation beams L1 into the light-guiding layer 60.

The top layer 70 is disposed on the bottom layer 50. The top layer 70 includes a grid portion 71 and a number of guiding portions 72. The grid portion 71 and the guiding portions 72 are disposed on the light-guiding layer 60.

As shown in FIGS. 2 and 3, the grid portion 71 is surrounding the guiding portions 72, and the guiding portions 72 are arranged in an array. Each of the wells B12 is located over one of the guiding portions 72.

In some embodiments, the refractive index of the bottom layer 50 is in a range from about 1 to about 1.5. The refractive index of the light-guiding layer 60 is in a range from about 1.5 to about 3. The refractive index of the guiding portion 72 is in a range from about 1.5 to about 3. The refractive index of the grid portion 71 is in a range from about 1 to about 1.5.

In some embodiments, the refractive index of the light-guiding layer 60 is equal to the refractive index of the guiding portion 72. The light-guiding layer 60 and the guiding portion 72 are made from the same material and formed as a single piece.

In some embodiments, the refractive indexes of the light-guiding layer 60 and the guiding portion 72 are greater than the refractive indexes of the bottom layer 50.

In this embodiment, the light-guiding layer 60 is located between the bottom layer 50 and the top layer 70. The grid portion 71 is configured to reflect the excitation beam L1 in the light-guiding layer 60 by total internal reflection, and the bottom layer 50 is configured to reflect a portion of the excitation beam L1 in the light-guiding layer 60 by total internal reflection. Therefore, the excitation beam L1 can be transmitted along the light-guiding layer 60.

In addition, the microlens includes a refractive index in a range from about 1.4 to about 2.3. The excitation beam L1 directly transmitted to the microlens or reflected to the microlens by the grid portion 71 is reflected toward the wells B12 via the guiding portions 72 by the microlenses 40.

As shown in FIG. 2, the light source 4 emits the excitation beam L1. A portion of the excitation beam L1 is transmitted along light-guiding layer 60 by total internal reflection. Moreover, a portion of the excitation beam L1 is transmitted to the microlenses 40 and is reflected by the microlenses 40. Therefore, a portion of the excitation beam L1 reflected by the microlenses 40 are transmitted to the specimens B2 via the guiding portions 72 and the carrying body B11.

The specimen B2 emits induced beam L2 when the specimen B2 is irradiated by the excitation beam L1. A portion of the induced beam L2 is blocked by the grid portion 71. A portion of the induced beam L2 is transmitted to the image sensor 1 via the guiding portions 72 and the light-guiding layer 60 in sequence. When the induced beams L2 fall on the image sensor 1, the induced beams L2 are transmitted to the sensing layer 10 via the microlenses 40 and the filter units 30 in sequence.

The induced beams L2 are focused by the microlenses 40. Each of the filter units 30 allows a predetermined range of wavelengths of the induced beams L2 to pass. Each of the sensing units 12 generates a detection signal according to the induced beam L2 falling thereon.

For example, if the induced beam L2 is a red beam, the induced beam L2 can pass through the red filter unit 30a but is blocked by the filter unit 30b. Therefore, the sensing unit 12b corresponding to the red filter unit 30a generates a detection signal, but the sensing unit 12b corresponding to the filter unit 30b does not generate a detection signal. Since the sensing units 12a and 12b correspond to the specimen B2a and the wells B12a, the color of the induced beam L2 generated by the specimen B2a can be determined.

Since the detection device 100 is made by semiconductor manufacturing process, the size of the detection device 100 is small, and the weight of the detection device 100 is light. In some embodiments, the width or the length of the detection device 100 is in a range about 6.35 mm to about 12.7 mm, and the thickness of the detection device 100 is in a range about 3 um to about 4.5 um. Therefore, the detection device 100 is portable. Moreover, the manufacturing cost of the detection device 100 is cheaper than the conventional biochip detection device having a large amount of optical elements.

In addition, the image sensor 1 integrates with the light-guiding structure 2, and the image sensor 1 senses the induced beams L2 generated by the specimens B2 at the same time. Therefore, the time required for detection of the specimens B2 of the detection device 100 is decreased.

Figure 4:
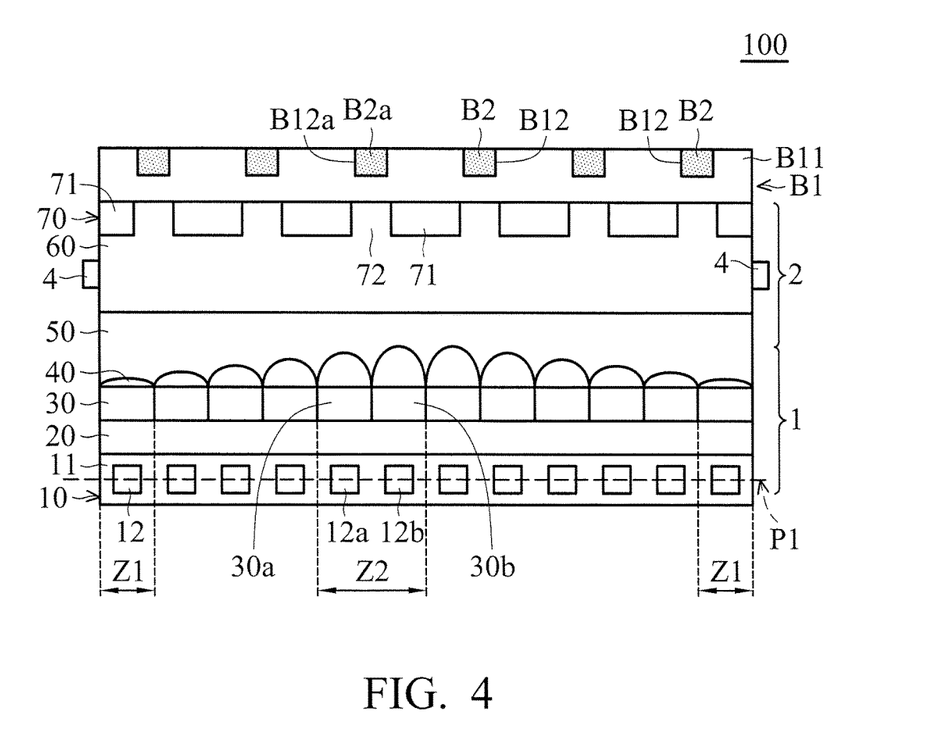
FIG. 4 is a schematic view of a detection device in accordance with a second embodiment of the present disclosure.

FIG. 4 is a schematic view of a detection device 100 in accordance with a second embodiment of the present disclosure. As shown in FIGS. 2 and 3, the heights of the microlenses 40 are gradually increased from an edge area Z1 of the detection device 100 to a central area Z2 of the detection device 100. By the structure of the light-guiding structure 2, the excitation beam L1 transmitted to the wells B12 and the specimens B2 are more uniform.

Figure 5:
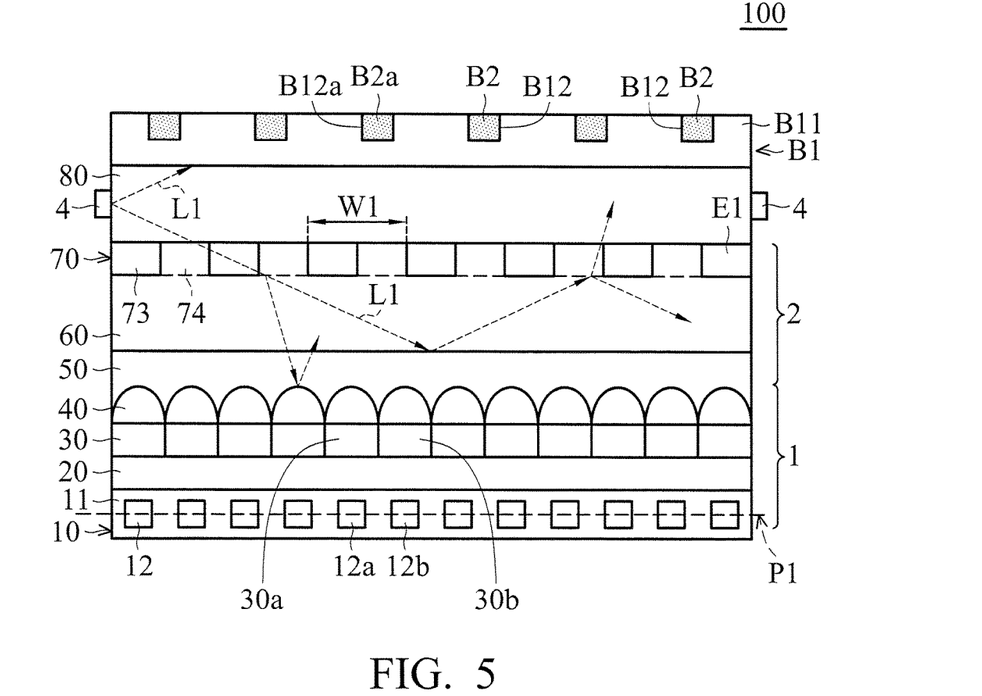
FIG. 5 is a schematic view of a detection device in accordance with a third embodiment of the present disclosure.

FIG. 5 is a schematic view of a detection device 100 in accordance with a third embodiment of the present disclosure. The light-guiding structure 2 further includes a transmitting layer 80 disposed on the top layer 70. The carrier B1 is disposed on the transmitting layer 80. The light source 4 is disposed on a side surface of the transmitting layer 80 and configured to emit an excitation beam L1 into the transmitting layer 80.

A portion of the excitation beam L1 in the transmitting layer 80 is directly transmitted to the specimens B2. The excitation beam L1 transmitted to the light-guiding structure 2 is scattered at an interface E1 of the light-guiding layer 60 and the top layer 70 or the top layer 70 when the excitation beam L1 passes through the top layer 70 into the light-guiding layer 60.

A portion of the excitation beam L1 in the light-guiding layer 60 is reflected by the bottom layer 50, and a portion of the excitation beam L1 in the light-guiding layer 60 is transmitted toward the microlenses 40. The excitation beam L1 reflected by the bottom layer 50 may be transmitted to the interface E1 and scattered at the interface E1 or the top layer 70. A portion of the excitation beam L1 scattered at the interface E1 or the top layer 70 may be transmitted toward the specimen B2 or reflect by the interface E1.

The top layer 70 includes a number of the first grating portions 73 and a number of second grating portions 74 arranged alternately. In some embodiments, the first grating portions 73 and the second grating portions 74 are rod structures parallel to each other.

In some embodiments, the wells B12 are not aligned with the first grating portions 73 (or the second grating portions 74). As shown in FIG. 5, each of the first grating portions 73 (or the second grating portions 74) has an offset to a nearest well of the wells B12 in a direction perpendicular to the top layer 70, and the offsets are varied. In other words, some of the centers of the wells B12 are respectively located over some of the centers of the first grating portions 73 (or second grating portions 74), and some of the centers of the wells B12 are not located over some of the centers of the first grating portions 73 (or second grating portions 74).

In some embodiments, the wells B12 are aligned with the first grating portions 73 (or the second grating portions 74). Each of the first grating portions 73 (or the second grating portions 74) has an offset to a nearest well of the wells B12 in a direction perpendicular to the top layer 70, and the offsets are the same. In other words, each of the wells B12 is located over one of the first grating portions 73 (or the second grating portions 74). In some embodiments, each of the centers of the wells B12 is respectively located over each of the centers of the first grating portions 73 (or second grating portions 74). In some embodiments, the wells B12 are not located over the second grating portions 74 (or the first grating portions 73).

The refractive index of the first grating portions 73 is lower than the refractive index of the second grating portions 74. In some embodiments, the refractive index of the light-guiding layer 60 is about 1 to 1.5 times the refractive indexes of the transmitting layer 80 and the first grating portions 73.

In some embodiments, the refractive index of the transmitting layer 80 is equal to the refractive index of the first grating portions 73. The transmitting layer 80 and the first grating portions 73 are made from the same material and are formed as a single piece.

In some embodiments, the refractive index of the light-guiding layer 60 is equal to the refractive index of the second grating portions 74. The light-guiding layer 60 and the second grating portions 74 are made from the same material and formed as a single piece.

The thickness of the transmitting layer 80 is about 8 times to about 200 times the thickness of the light-guiding layer 60, and the thickness of the light-guiding layer 60 is about 1 times to about 2 times the thickness of the top layer 70.

In some embodiments, the width W1 of the first grating portion 73 and the second grating portion 74 adjacent to the first grating portion 73 is in range from about one-quarter of the wavelength of the excitation beam L1 to about half the wavelength of the excitation beam L1.

In some embodiments, the thickness of the transmitting layer 80 is in a range from about 8 um to about 200 um. The thickness of the light-guiding layer 60 is in a range from about 0.6 um to about 2 um. The thickness of the first grating portions 73 and the second grating portions 74 of the top layer 70 is in a range from about 0.1 um to about 0.5 um.

Accordingly, by the structure of the light-guiding structure 2, most of the excitation beam L1 can be transmitted to the specimens B2.

The microlenses 40 are configured to reflect the excitation beam L1 toward the wells B12 via the bottom layer 50, the light-guiding layer 60, the top layer 70, and the transmitting layer 80 in sequence The induced beams L2 are transmitted to the image sensor 1 via the transmitting layer 80, the top layer 70, the light-guiding layer 60, and the bottom layer 50 in sequence.

Figure 6:
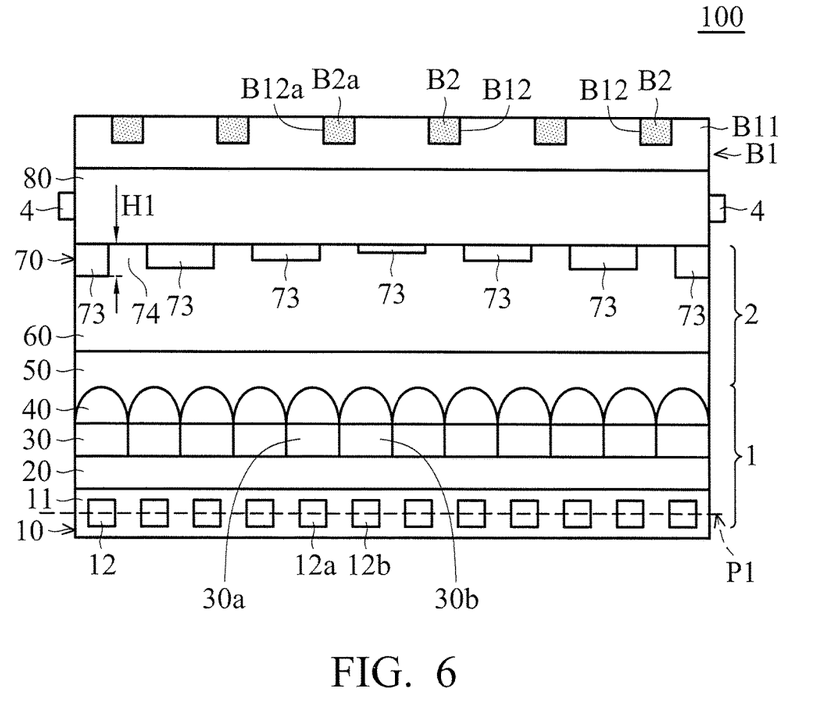
FIG. 6 is a schematic view of a detection device in accordance with a fourth embodiment of the present disclosure.

FIG. 6 is a schematic view of a detection device 100 in accordance with a fourth embodiment of the present disclosure. The heights H1 relative to the transmitting layer 80 of the first grating portions 73 are gradually decreased from the edge area of the light-guiding structure 2 to the central area of the light-guiding structure 2. Therefore, by the structure of the first grating portions 73, the excitation beam L1 transmitted to the wells B12 and the specimens B2 are more uniform.

Figure 7:
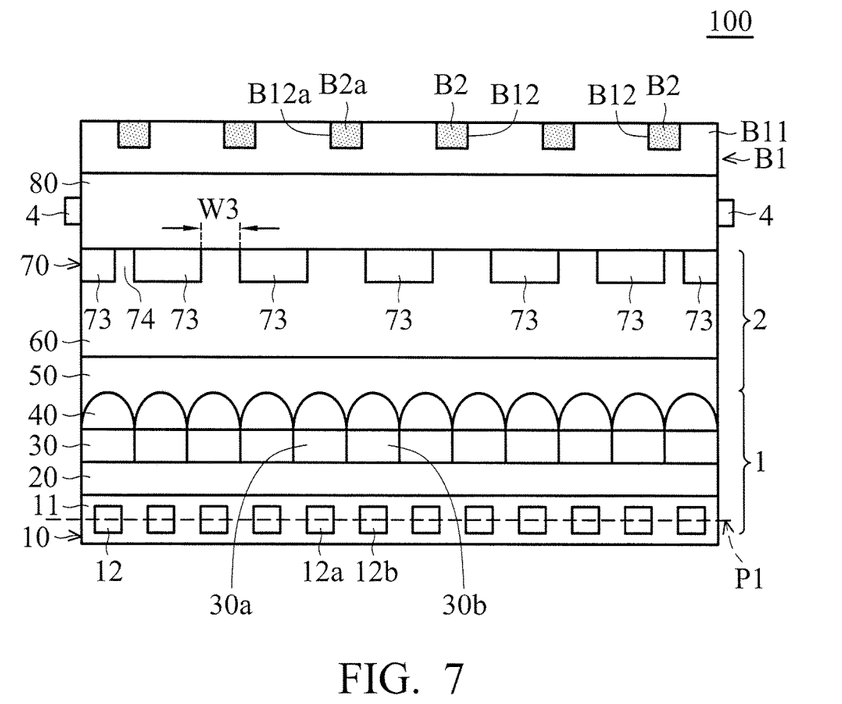
FIG. 7 is a schematic view of a detection device in accordance with a fifth embodiment of the present disclosure.

FIG. 7 is a schematic view of a detection device 100 in accordance with a fifth embodiment of the present disclosure. The intervals W3 between two adjacent first grating portions 73 are gradually increased from the edge area of the light-guiding structure 2 to the central area of the light-guiding structure 2. Therefore, by the structure of the first grating portions 73, the excitation beam L1 transmitted to the wells B12 and the specimens B2 are more uniform.

Figure 8:
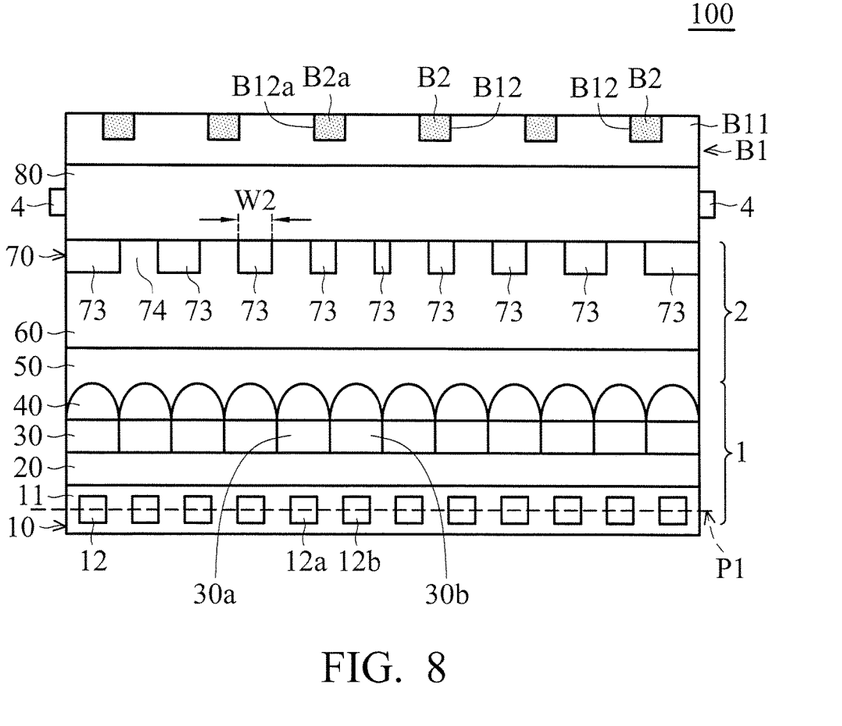
FIG. 8 is a schematic view of a detection device in accordance with a sixth embodiment of the present disclosure.

FIG. 8 is a schematic view of a detection device 100 in accordance with a sixth embodiment of the present disclosure. The widths W2 of the first grating portions 73 are gradually decreased from the edge area of the light-guiding structure 2 to the central area of the light-guiding structure 2. Therefore, by the structure of the first grating portions 73, the excitation beam L1 transmitted to the wells B12 and the specimens B2 are more uniform.

In conclusion, since the detection device is integrated with the image sensor and the light-guiding structure, the size and the weight of the detection device are greatly decreased, and the manufacturing cost of the detection device is cheap. Moreover, the specimens on the carrier can be detected by the image sensor at the same time, and the thus the time required for detection of the specimens is decreased.

While the invention has been described by way of example and in terms of preferred embodiment, it is to be understood that the invention is not limited thereto. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A detection device for specimens, comprising:
   an image sensor;
   a light-guiding structure, disposed on the image sensor, comprising:
      a light-guiding layer disposed on the image sensor; and
      a top layer disposed on the light-guiding layer;
   a carrier, disposed on the light-guiding structure, having a plurality of wells arranged in a second array located over the top layer, wherein each of the wells is configured to receive and hold a specimen solely within the well, and
   a light source adjacent to a side surface of the light-guiding layer and configured to emit an excitation beam into the light-guiding layer, wherein a portion of the excitation beam is transmitted from the light source along the light-guiding layer to the plurality of wells and another portion of the excitation beam is transmitted from the light source to the microlenses and is reflected by the microlenses to the plurality of wells,
   wherein the top layer includes a plurality of guiding portions, disposed on the light-guiding layer, arranged in a first array, and the wells located over the guiding portions,
   wherein the excitation beam is transmitted to the specimens via the top layer,
   wherein the carrier comprises a top surface and a bottom surface and the plurality of wells is arranged in contact with the top surface of the carrier and the bottom surface of the carrier is opposite of the top surface, and
   wherein the specimens emit induced beams when the specimens are irradiated by the excitation beam, and the detection device is configured so that the induced beams are transmitted from at least one well then through the bottom surface of the carrier and then to the image sensor via the top layer and the light-guiding layer, in sequence.

2. The detection device for specimens as claimed in claim 1, wherein the image sensor comprises:
a sensing layer;
a plurality of filter units, disposed on the sensing layer, arranged in a third array; and
a plurality of microlenses, disposed on the filter units, arranged in a fourth array,
wherein the light-guiding structure is disposed on the microlenses, and the microlenses are configured to reflect the excitation beam toward the wells,
wherein the induced beams are transmitted to the sensing layer via the microlenses and the filter units in sequence.

3. The detection device for specimens as claimed in claim 2, wherein the image sensor further comprises a cutting layer, disposed between the sensing layer and the microlenses, configured to block the excitation beam passing through to the sensing layer.

4. The detection device for specimens as claimed in claim 2, wherein each of the microlenses has a greatest height, and the greatest heights of the microlenses gradually increases from an edge area of the detection device to a central area of the detection device so that the microlenses closest to the central area have a largest greatest height and the microlenses closest to the edge area have a smallest greatest height.

5. The detection device for specimens as claimed in claim 1, wherein the top layer further comprises a grid portion, surrounding the guiding portions, disposed on the light-guiding layer, wherein the grid portion is a portion of the top layer that is configured to reflect the excitation beam in the light-guiding layer.

6. The detection device for specimens as claimed in claim 5, wherein a refractive index of the light-guiding layer is greater than a refractive index of the grid portion.

7. The detection device for specimens as claimed in claim 1, wherein the light-guiding structure further comprises a bottom layer disposed on the image sensor, wherein the bottom layer is configured to reflect the excitation beam in the light-guiding layer.

8. The detection device for specimens as claimed in claim 7, wherein a refractive index of the light-guiding layer is greater than a refractive index of the bottom layer.

9. A detection device for specimens, comprising:
an image sensor comprising a plurality of micro lenses arranged in a first array;
a light-guiding structure, comprising:
a light-guiding layer disposed on the micro lenses; and
a top layer disposed on the light-guiding layer;
a carrier, disposed on the light-guiding structure, having a plurality of wells arranged in a second array located over the top layer, wherein each of the wells is configured to receive and hold a specimen solely within the well, and
a light source adjacent to a side surface of the light-guiding layer and configured to emit an excitation beam into the light-guiding layer, wherein a portion of the excitation beam is transmitted from the light source along the light-guiding layer to the plurality of wells and another portion of the excitation beam is transmitted from the light source to the microlenses and is reflected by the microlenses to the plurality of wells,
wherein the top layer includes a plurality of guiding portions, disposed on the light-guiding layer, arranged in a first array, and the wells located over the guiding portions,
wherein the excitation beam is transmitted to the specimens via the top layer,
wherein the carrier comprises a top surface and a bottom surface and the plurality of wells is arranged in contact with the top surface of the carrier and the bottom surface of the carrier is opposite of the top surface, and
wherein the specimens emit induced beams when the specimens are irradiated by the excitation beam, and the detection device is configured so that the induced beams are transmitted from at least one well then through the bottom surface of the carrier and then to the image sensor via the top layer and the light-guiding layer, in sequence.

10. The detection device for specimens as claimed in claim 9, wherein the image sensor comprises:
a sensing layer; and
a plurality of filter units, disposed on the sensing layer, arranged in a third array;
wherein the microlenses are disposed on the filter units, and the induced beams are transmitted to the sensing layer via the microlenses and the filter units in sequence.

11. The detection device for specimens as claimed in claim 9, wherein the top layer comprises a plurality of the first grating portions and a plurality of second grating portions, and each of the first grating portions and each of the second grating portions are arranged alternately.

12. The detection device for specimens as claimed in claim 11, wherein heights of the first grating portions relative to the transmitting layer are gradually decreased from an edge area of the light-guiding structure to a central area of the light-guiding structure.

13. The detection device for specimens as claimed in claim 11, wherein widths of the first grating portions are gradually decreased from an edge area of the light-guiding structure to a central area of the light-guiding structure.

14. The detection device for specimens as claimed in claim 11, wherein intervals between two adjacent first grating portions are gradually increased from an edge area of the light-guiding structure to a central area of the light-guiding structure.

15. The detection device for specimens as claimed in claim 11, wherein a refractive index of the first grating portions is greater than a refractive index of the second grating portions, and a refractive index of the light-guiding layer is greater than a refractive index of the transmitting layer and the first grating portions.

16. The detection device for specimens as claimed in claim 11, wherein each of the first grating portions has an offset to a nearest well of the wells in a direction perpendicular to the top layer, and the offsets are varied.

* * * * *